United States Patent [19]

Chive et al.

[11] Patent Number: 5,354,325
[45] Date of Patent: Oct. 11, 1994

[54] SYSTEM FOR INTERNAL HEAT TREATMENT OF A SPECIFIC BODY AND ITS USE

[75] Inventors: Maurice Chive, Villeneuve d'Ascq; Jean-Pierre Sozanski, Thumeries; Yves Moschetto, Haubourdin; Daniel Vanloot, Calais, all of France

[73] Assignees: Institut National de la Sante et de la Recherche Medicale; Universite des Sciences et Technologies de Lille, both of Paris, France

[21] Appl. No.: 30,247

[22] PCT Filed: Jul. 23, 1992

[86] PCT No.: PCT/FR92/00729

§ 371 Date: Mar. 15, 1993

§ 102(e) Date: Mar. 15, 1993

[87] PCT Pub. No.: WO93/02747

PCT Pub. Date: Feb. 18, 1993

[30] Foreign Application Priority Data

Jul. 26, 1991 [FR] France .................. 91 09521

[51] Int. Cl.5 .............................. A61N 5/00
[52] U.S. Cl. ................... 607/101; 607/102; 607/154
[58] Field of Search ............... 607/101, 102, 154–156; 219/10.55 A, 10.55 F

[56] References Cited

U.S. PATENT DOCUMENTS

| 4,632,128 | 12/1986 | Paglione et al. | 219/10.55 R |
| 4,785,829 | 11/1988 | Convert et al. | 607/101 |
| 4,798,215 | 1/1989 | Turner | 607/102 |
| 5,007,437 | 4/1991 | Sterzer | 607/156 |
| 5,033,478 | 7/1991 | Kikuchi et al. | 607/102 |

FOREIGN PATENT DOCUMENTS

WO88/03823 6/1988 European Pat. Off. .
0370890 5/1990 European Pat. Off. .
0485323 5/1992 European Pat. Off. ............ 607/102
2650390 3/1986 France .

OTHER PUBLICATIONS

Mendecki et al. "Microwave Applicators For Localized Hyperthermia Treatment of Cancer of the Prostate" *Int. J. Radiation Oncology Biol. Phys.* vol. 6, No. 11 pp. 1583–1585, Nov. 1980.
Database WPIL, Week 8819, Derwent Publ. Ltd., London GB; AN 88-132135 & SU,A, 1,345,142 (Ioselson) Oct. 15, 1987 –see abstract.
Database WPIL, Week 9103, Derwent Publ. Ltd., London GB; AN 91-020869 & SU,A, 1,567,203 (Koleshko) May 30, 1990 –see abstract.

*Primary Examiner*—Lee S. Cohen
*Assistant Examiner*—Robert L. Nasser, Jr.
*Attorney, Agent, or Firm*—Larson and Taylor

[57] ABSTRACT

A system for internal heat treatment of specific bodies by microwave including a generator 1 of microwave energy at a frequency f0, at least one channel for transmission of the microwave energy, each channel making it possible to generate a modulated microwave treatment signal, the wave of the microwave energy of two consecutive channels exhibiting a phase shift of defined value. At least one microwave applicator is associated with one of the channels in order to ensure application of the microwave energy delivered by this channel at separate adjacent points of the area Z to be treated, and a dual-temperature-reference radiometer is interconnected selectively to the applicator which then plays the role of temperature sensor, the absolute temperature of the adjacent point of the area Z to be treated being thus determined. The microwave powers radiated and the instantaneous temperatures of the separate points of the area Z to be treated are displayed. Application to treatments by hyperthermia, especially of living tissues.

14 Claims, 7 Drawing Sheets

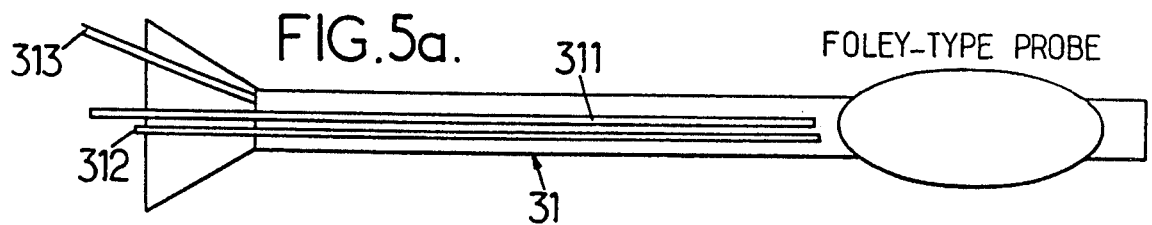
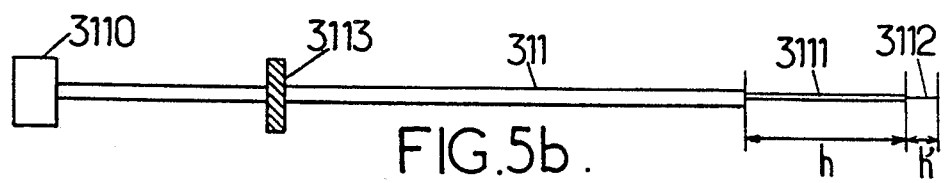
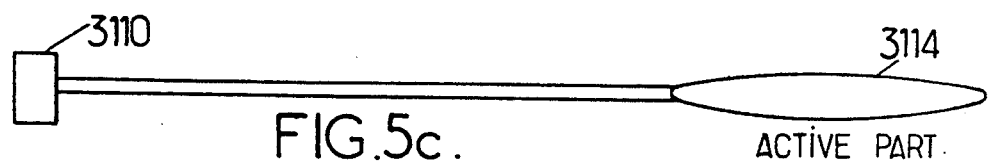
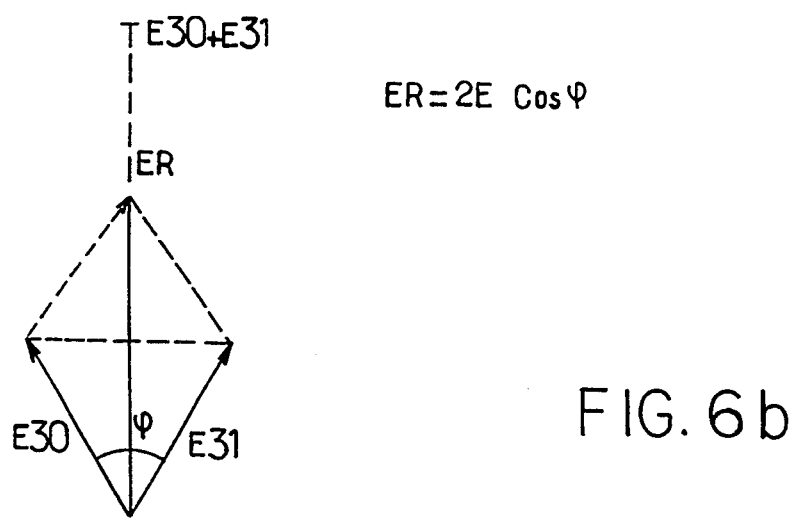
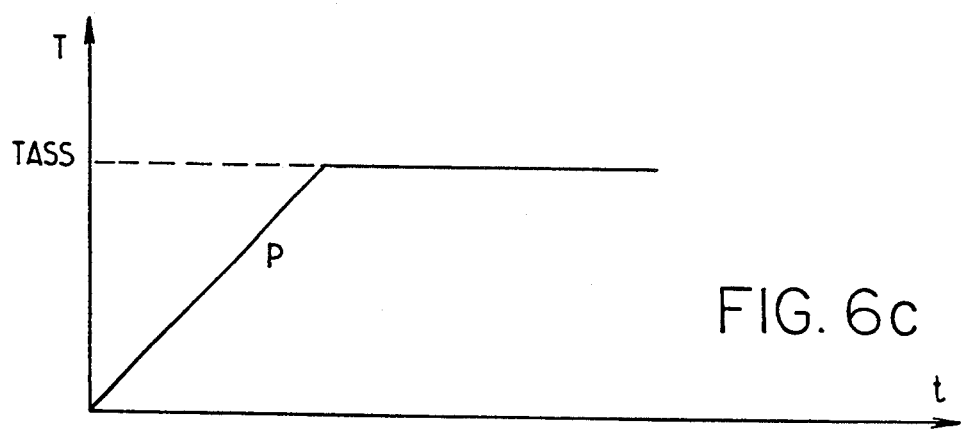

SYSTEM FOR INTERNAL HEAT TREATMENT OF A SPECIFIC BODY AND ITS USE

The invention relates to a system for the internal heat treatment of a specific body and to the use of this system.

The internal heat treatment appliances are normally used either in industrial processes or, according to a novel trend, in methods of therapeutic treatment by hyperthermia.

In the two abovementioned cases, an essential element of these types of appliances is precision as much in the temperature as in the field of application, with respect to the area to be treated, of the hyperthermia generated.

When such operational modes are employed, especially with a view to heat treatment of a specific body, such as the human body for example, a method consists in introducing, into a natural cavity of the latter, an element for emitting and/or concentrating energy, such as microwave electromagnetic energy, the dissipative nature of the walls of this cavity, seats of a resultant electric field being then subjected to a corresponding rise in temperature.

Such an operational mode, although capable of giving satisfaction, does not make it possible to establish with sufficient precision the temperature effectively reached by the area to be treated, or the region of the specific body and hence of the area to be treated in this region subjected to the hyperthermia generated, except by providing one or more temperature sensors arranged in the vicinity of the abovementioned area.

In the case where the specific body subjected to the treatment is the human body, it goes without saying that the use of a natural cavity so as to carry out implantation of abovementioned temperature sensors may be envisaged. But such an operating mode then exhibits the drawback of occupying the corresponding natural cavity, which practically prohibits the use of the latter for the implantation of a source or of a concentrator element for hyperthermia-generating energy. In such a case, the closely spaced nature of two adjacent natural cavities cannot be used to bring about, for example, treatment by hyperthermia of an area to be treated which is situated between the latter.

Furthermore, it will be noted that the use of temperature sensors placed in the vicinity of the electromagnetic energy source element generating the hyperthermia may be inimical to the operation of these sensors, especially by reason of the fact that the active semiconductor elements of the latter are capable of being subjected, in the course of operation, to an intense electric field.

The object of the present invention is to remedy the series of abovementioned drawbacks by implementing a system for the internal heat treatment of specific bodies, by application of microwave energy, making it possible to obtain satisfactory precision as much in the temperature reached as in the region in which the hyperthermia is generated.

Another object of the present invention is the implementation of the system for the internal heat treatment of specific bodies, by application of microwave energy, in which one or more microwave energy applicators are provided, this or these applicators being, in addition to their applicator function, intended to play the role of temperature sensor in the temporary absence of microwave energy application, which makes it possible to take a measurement of the instantaneous temperature at separate points in the vicinity of the area to be treated, these points corresponding exactly to the points of application of the microwave energy in the vicinity of the area to be treated.

Another subject of the present invention finally is the implementation of a system for the internal heat treatment of specific bodies, by application of microwave energy, this system, by virtue of a large dynamic range of level of power radiated in the vicinity of the area to be treated, exhibiting great flexibility in use for very varied applications.

The system for the internal heat treatment of specific bodies by application of microwave energy, which is the subject of the present invention, is noteworthy in that it comprises a generator of microwave energy at a defined frequency, at least one channel for transmission of the microwave energy emitted by the generator, each channel making it possible to generate a microwave treatment signal modulated in amplitude according to a periodic modulation law of frequency f1, the carrier wave of the microwave energy of two consecutive channels exhibiting a phase shift of defined value. One microwave applicator at least is associated with at least one channel and makes it possible to ensure application of the microwave energy delivered by this channel at separate points in the vicinity of the area to be treated, and a dual-temperature-reference radiometer is interconnected selectively to this microwave applicator, playing the role of sensor and making it possible to measure the absolute temperature of the corresponding separate point in the vicinity of the area to be treated. A console for calculation and display of the microwave powers radiated and of the instantaneous temperatures of the separate points of the area to be treated is provided.

The system for the internal heat treatment of specific bodies which is the subject of the invention finds an application especially in the treatment of living tissues, in the non-limiting cases of ademona of the prostate, or intra-uterine menorrhagia or the like.

A more detailed description of a system for the internal heat treatment of a specific body and of the use of the latter will be given in connection with the description below and the drawings in which.

Figure 3A:
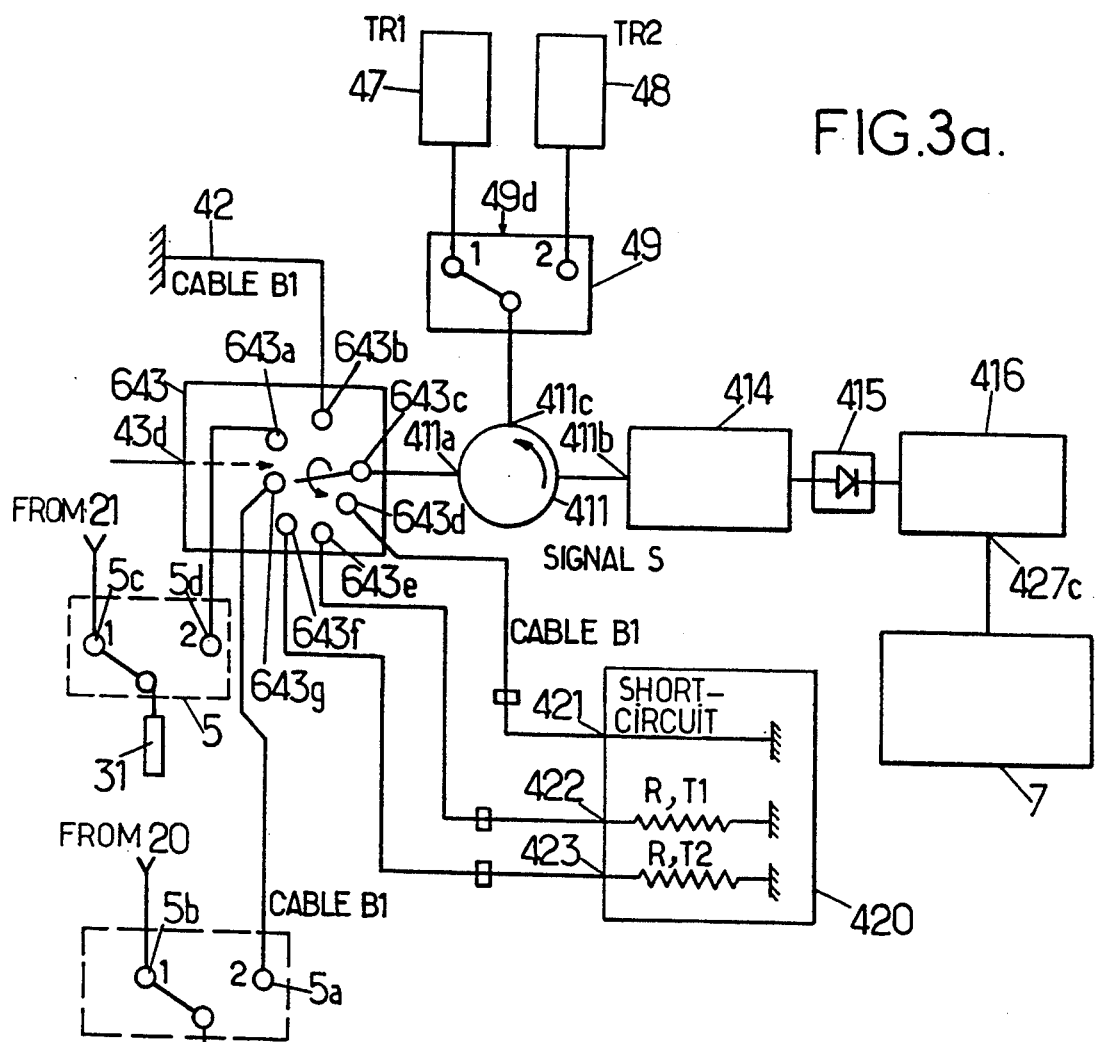
FIG. 3a represents an advantageous non-limiting embodiment of a dual-temperature-reference radiometer capable of being used for implementing a system for the internal heat treatment of a specific body according to the invention as presented in FIG. 1.
Figure 3B:
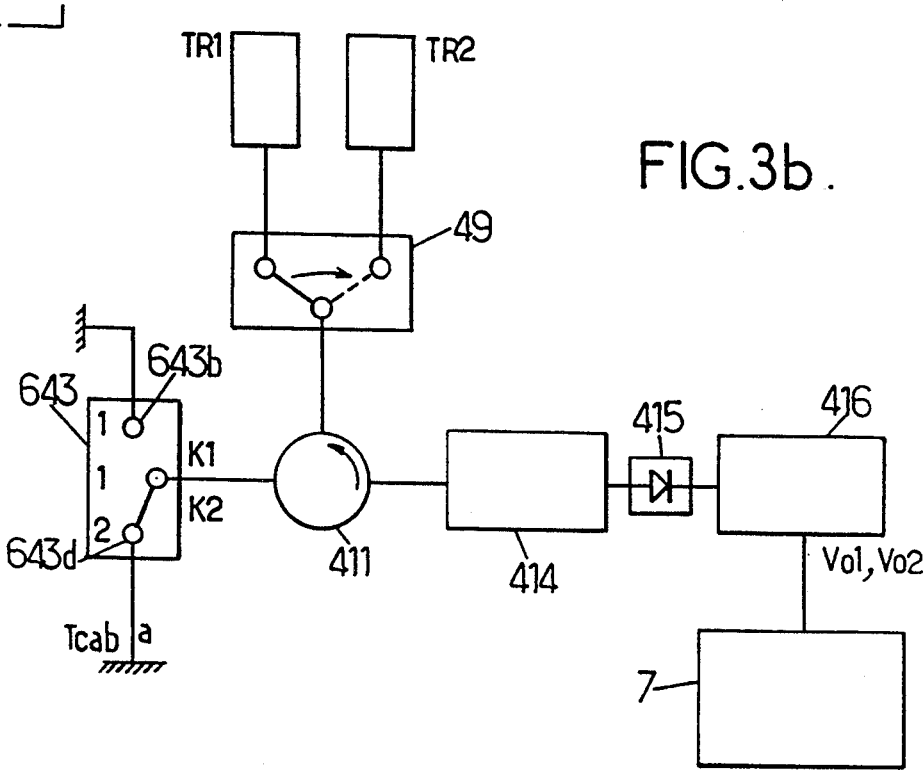
Figure 3C:
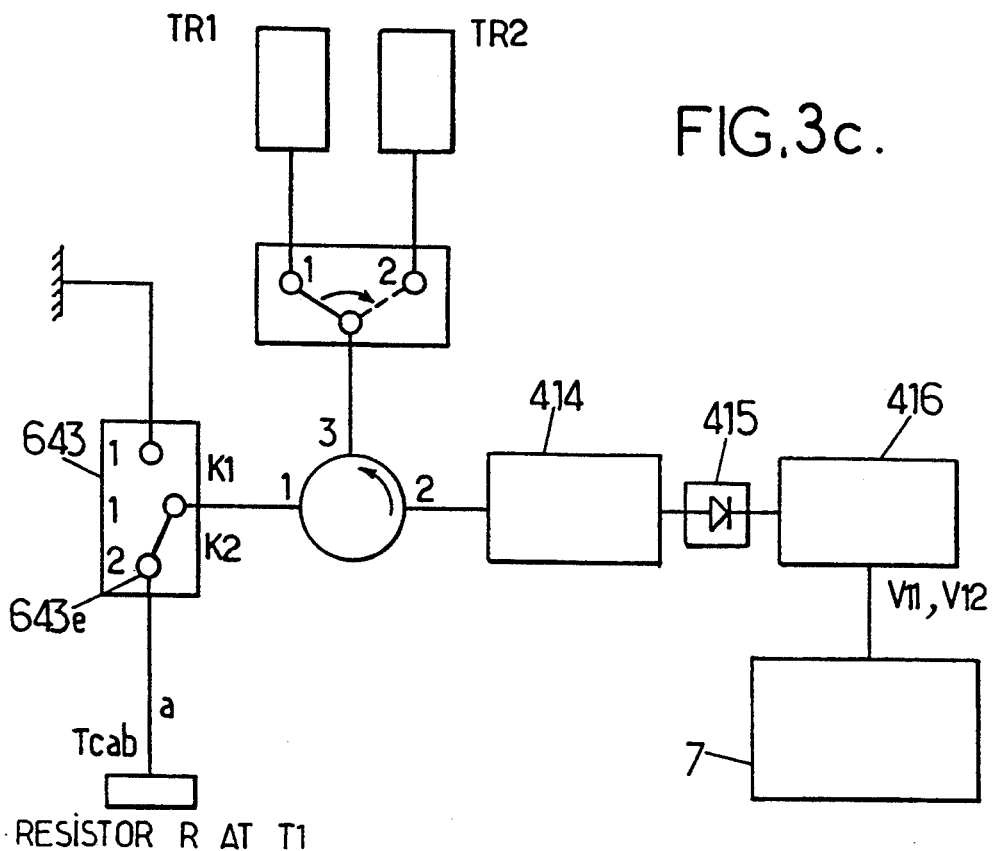
Figure 3D:
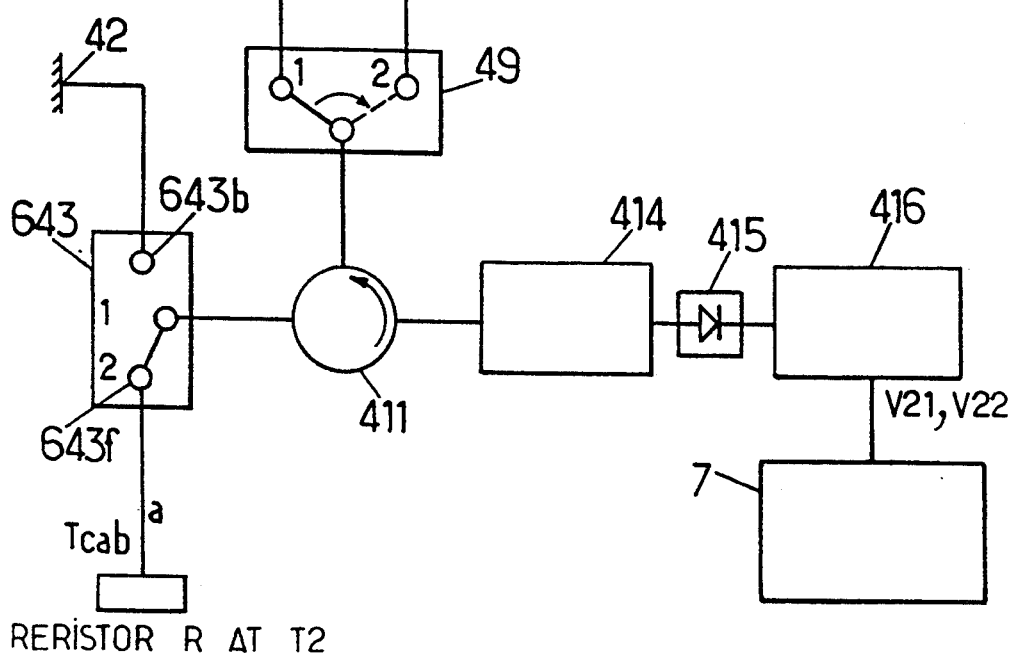
Figure 3E:
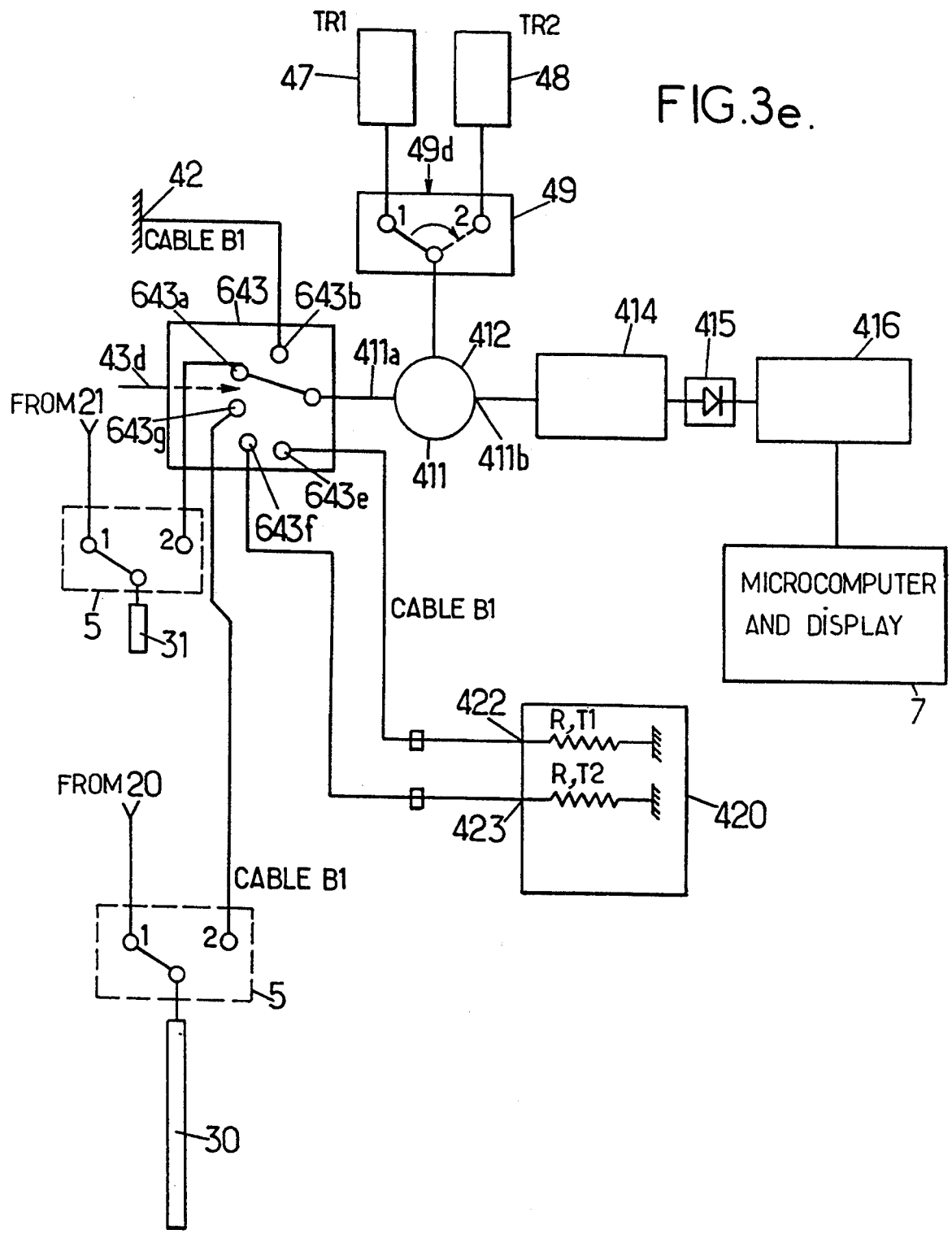
Figure 4:
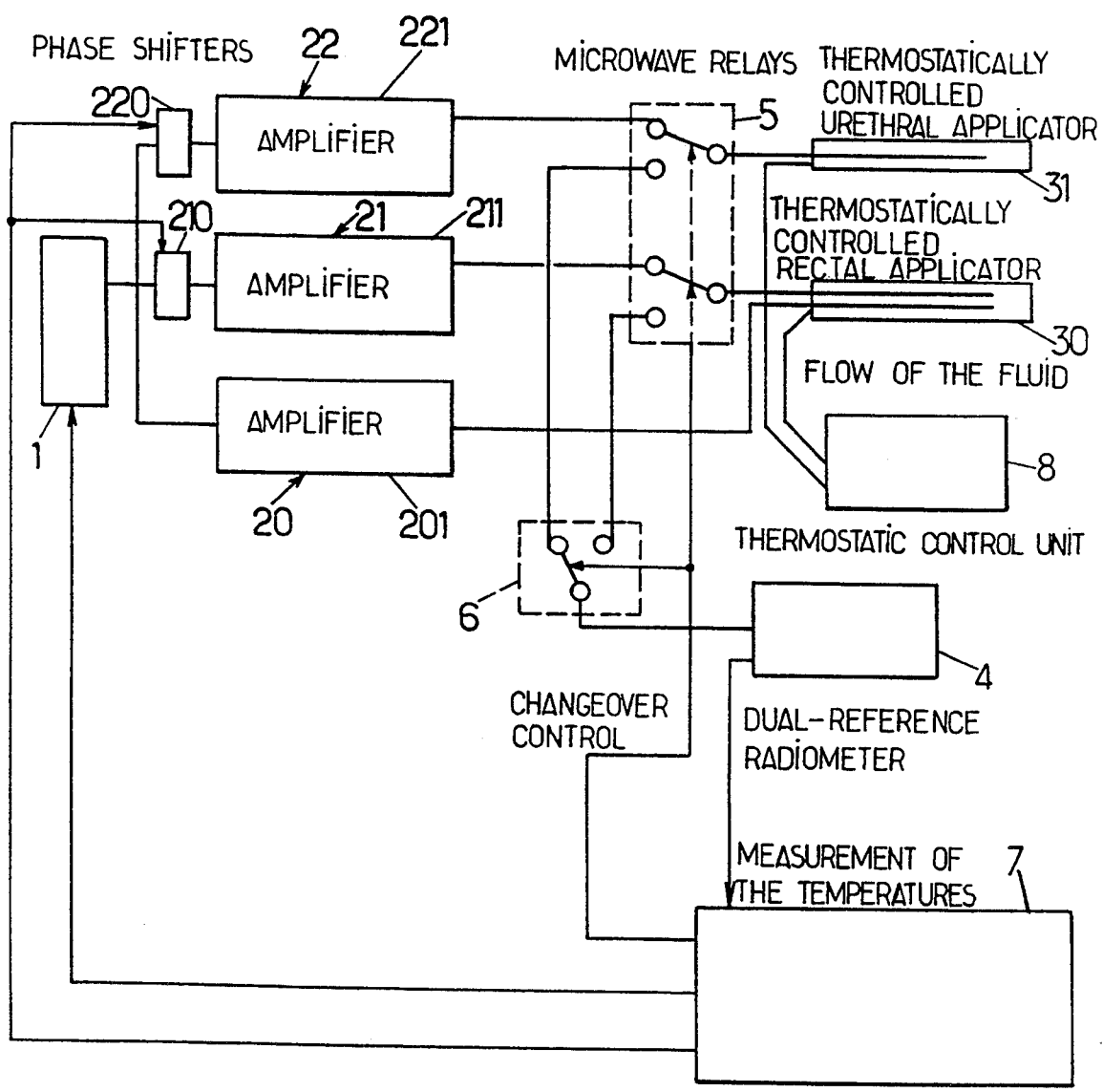
Figure 6A:
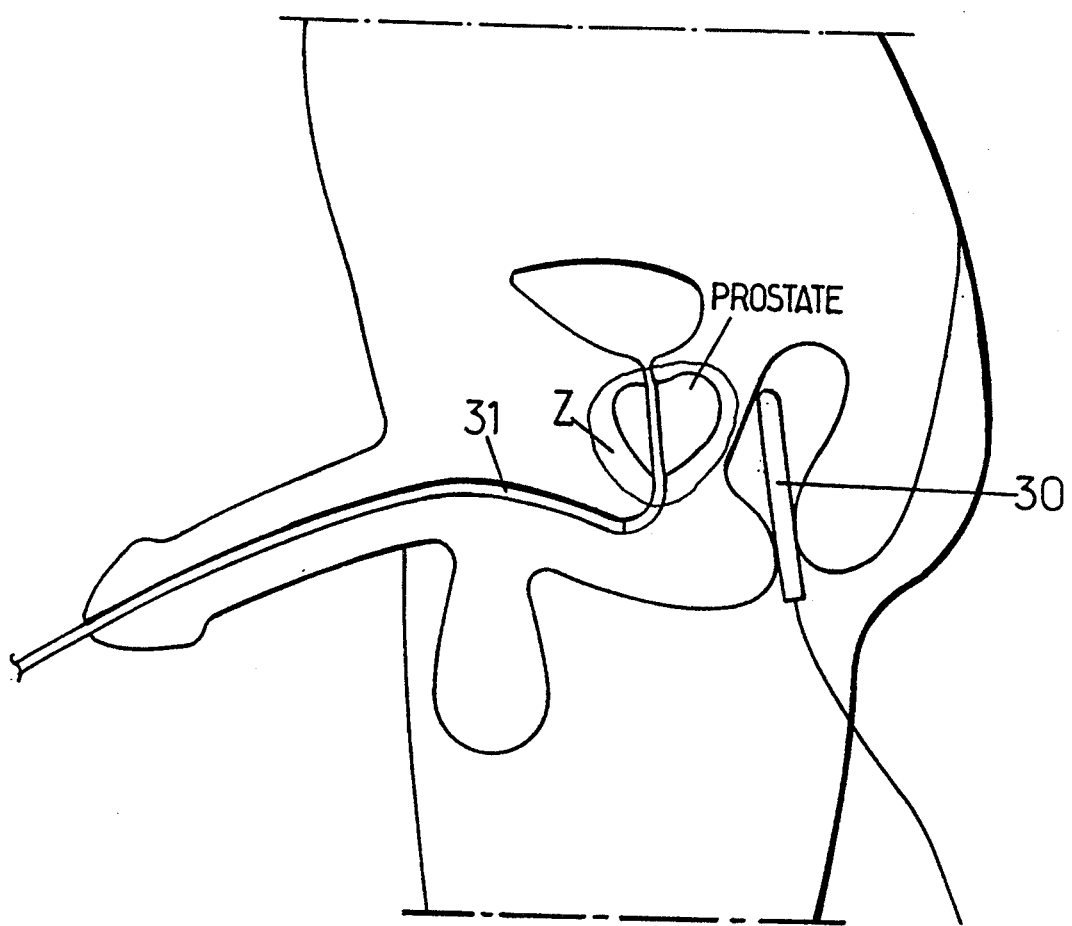

FIGS. 3b, 3c and 3d relate to the use of the system for the internal heat treatment of specific bodies, which is the subject of the invention, and in particular to a calibration process for this system, under best calibration precision conditions, prior to and/or in the course of a treatment session;

FIG. 3e represents an embodiment of the dual-temperature-reference radiometer as represented in FIG. 3a;

FIG. 4 represents an advantageous, non-limiting embodiment of a system for the internal heat treatment of a specific body, more particularly adapted to the treatment of ademona of the prostate;

FIGS. 5a, 5b and 5c relate to various embodiments of microwave energy applicators, also capable of playing the role of temperature sensor, in accordance with an essential characteristic of the subject of the invention;

FIG. 6a relates to the use of the system for the internal heat treatment of specific bodies according to the invention, in the case of the treatment of living tissues, with a view to reducing an adenoma of the prostate.

FIGS. 6b and 6c relate to the use of the system for the internal heat treatment of specific bodies according to the invention in a general case, and especially in the case of FIG. 6a.

A more detailed description of a system for the internal heat treatment of specific bodies by application of microwave energy to an area to be treated, in accordance with the subject of the present invention, will be given in connection with FIG. 1.

In a general way, as represented in the abovementioned figure, the system which is the subject of the present invention comprises a generator 1 of microwave energy at a defined frequency f0. The generator 1 may consist of an oscillator delivering a progressive wave at the frequency of 915 MHz, for example.

Figure 1:
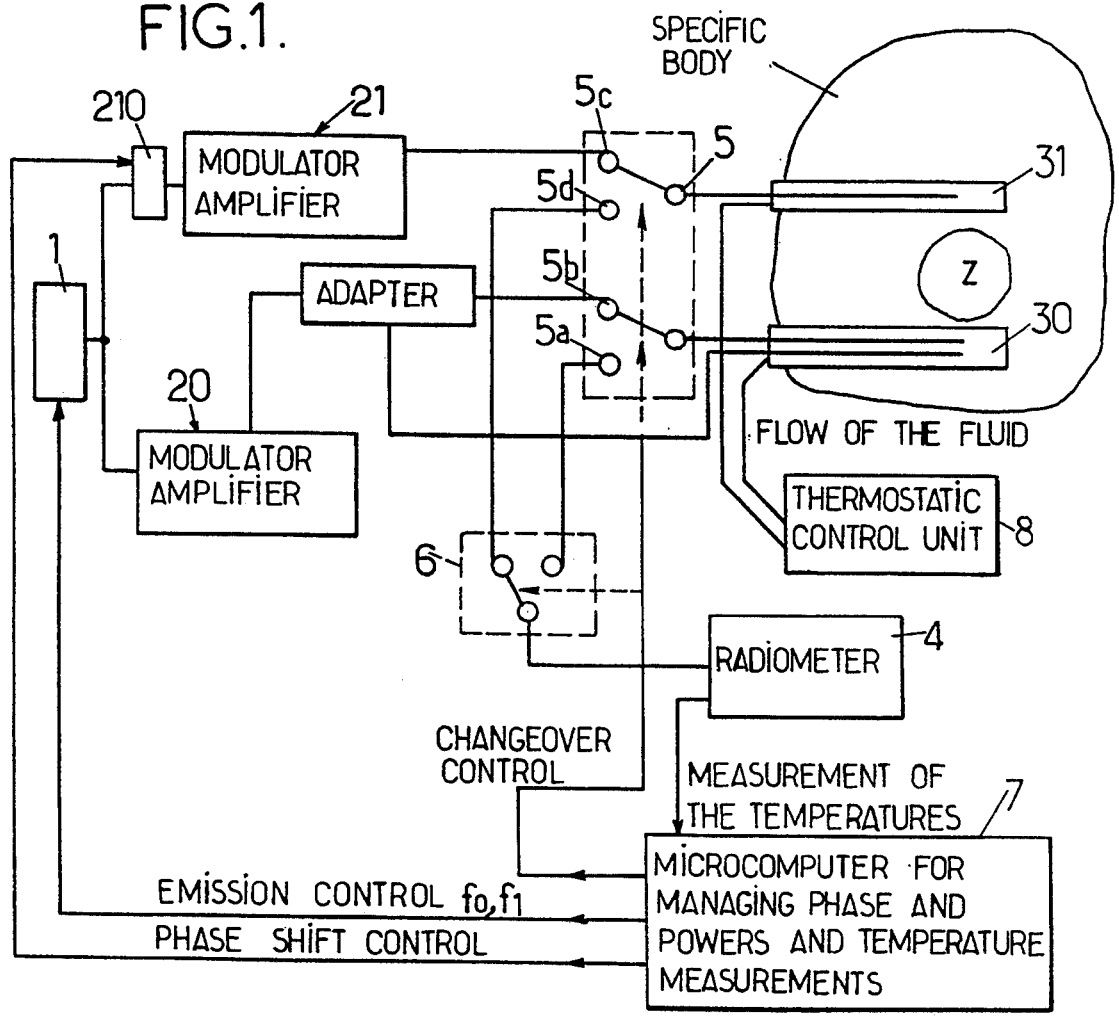
FIG. 1 represents a block diagram of a system for the internal heat treatment of a specific body according to the invention.

The system also comprises, as is represented in the abovementioned FIG. 1, at least one channel, marked 20, 21, for transmission of the microwave energy emitted by the generator 1. Each channel makes it possible to generate a microwave treatment signal modulated in amplitude according to a defined periodic modulation law of frequency f1. The channels 20 and 21 constituted by an amplifier with which an amplitude modulator, for example, is associated are represented in a non-limiting way in FIG. 1.

According to a particularly advantageous characteristic of the system which is the subject of the present invention, the carrier wave of the microwave energy of 2 consecutive channels, the channels 20 and 21 in FIG. 1, exhibit a phase shift of defined value.

As will be described in more detail in the description, the phase shift introduced at the level of the carrier wave transmitted by two consecutive channels in fact makes it possible to obtain a very large dynamic range in the microwave energy applied to the area Z to be treated.

As has furthermore been represented in FIG. 1, the system which is the subject of the present invention comprises at least one microwave applicator 30, 31, associated with at least 1 channel. The applicator 30 is, for example, associated with the channel 20, while the applicator 31 is associated with the channel 21. Each applicator thus makes it possible to ensure application of the microwave energy delivered by the corresponding channel at separate points in the vicinity of the area Z to be treated.

According to the particularly advantageous characteristic of the system, which is the subject of the present invention, the latter comprises a dual-temperature-reference radiometer 4. The radiometer 4 may be connected selectively to one or the other of the microwave sensors 30, 31, each applicator then playing the role of temperature sensor and thus makes it possible to measure the absolute temperature of the corresponding separate point in the vicinity of the area Z to be treated.

FIG. 1 shows the selective interconnection of the dual-temperature-reference radiometer 4 to one and/or to the other applicators 30, 31, by means of a first multichannel microwave changeover switch 5 and of a second multichannel microwave changeover switch 6. The use of two multichannel microwave changeover switches 5 and 6, as represented in FIG. 1, does not in any way prejudice the use of a single multichannel microwave changeover switch to provide a similar function.

As has further been represented in FIG. 1, the system which is the subject of the present invention comprises a console for calculation and display of the microwave powers radiated and of the instantaneous temperatures of the separate points of the area Z to be treated. It will obviously be noted that the calculation and display console 7 comprises, for example, a microcomputer equipped with its peripheral resources, this microcomputer being interconnected, on the one hand, to the microwave energy generator 1 so as to control the emission of the carrier wave of the microwave signal tasked with delivering the thermal treatment energy, to one or more phase shifting circuits such as the circuit 210 represented on the transmission channel 21, the phase shift being controlled by means of the microcomputer of the calculation and display console 7 as a function of the applications in question, as will be described later in the description. Furthermore, as will be easily understood, the calculation and display console 7 makes it possible to control, by means of an interconnection, the microwave changeover switches 5 and 6 in such a way as to provide for the changeover switching of the applicators 30 and 31 for example, either in connection with the dual-temperature-reference radiometer 4, or in connection with the respective channels 20 or 21.

It will thus be noted that the operation of the system which is the subject of the present invention is particularly simplified with respect to the device of the prior art to the extent that the applicator or applicators 30 or 31 also forming temperature sensors, their installation as a function of the application in question is not hampered by the necessary implantation of separate temperature sensors, which, needless to say, makes it possible to conspicuously improve the precision of the treatment thus carried out, as much in the matter of the value of the temperature effectively produced in the area Z to be treated as in the measurement of this temperature at the effective application point of the microwave energy generating the hyperthermia.

One of the components making it possible to obtain the greatest precision relative to the temperature reached by the area Z to be treated consists, in accordance with one of the subjects of the present invention, in the use of a dual-temperature-reference radiometer 4.

A more detailed description of such a type of radiometer will be given in connection with FIG. 2.

According to the abovementioned figure, the dual-reference radiometer 4 may comprise a first microwave changeover switch 43 comprising two input channels marked 43a, 43b. These input channels are connected, one, 43a, to the output of an applicator by means of a multichannel microwave changeover switch, marked 43, and the other, 43b, to a microwave short-circuit, marked 42. An output 43c of the microwave changeover switch 43 may be connected to one or the other of the two abovementioned inputs.

Figure 2:
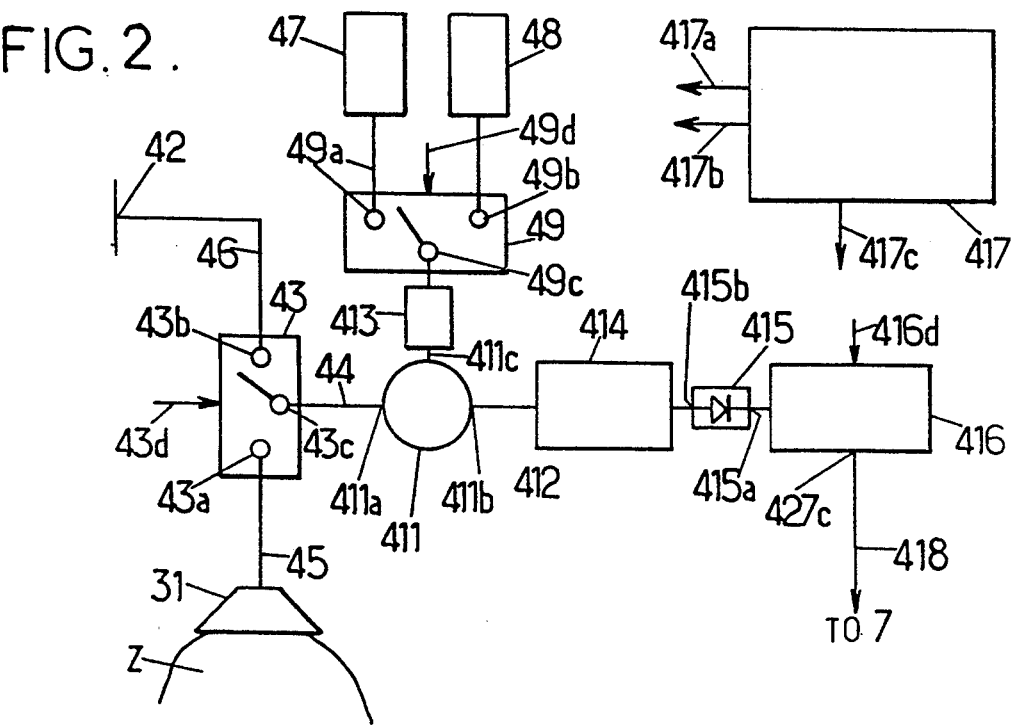
FIG. 2 represents a block diagram of an essential constituent element of the system which is the subject of the present invention as represented in FIG. 1, in this instance of a dual-temperature-reference radiometer.

As it has been represented in FIG. 2, the dual-temperature-reference radiometer 4 further comprises a circulator 411 comprising 3 channels, 411a, 411b, 411c. The first channel 411a is connected to the output of the first microwave changeover switch 43 and the second channel 411b is connected to the input of a microwave electronic treatment assembly marked 414, 415, 416, 417. The third channel 411c of the circulator 411 constitutes a reference input, that is to say an input receiving the signal delivered by one of the temperature references as will be described later in the description.

In FIG. 2 it may be observed that the dual-reference radiometer 4 also comprises at least 2 internal temperature reference sources, 47, 48, and a second microwave changeover switch, 49. The second microwave changeover switch 49 comprises at least two input channels, 49a and 49b, each connected to the output of one of the reference sources, 47, 48 respectively. The second microwave changeover switch 49 comprises an output 49c connected to the third reference input of the circulator 411c.

Furthermore, the dual-temperature-reference radiometer comprises a synchronization control circuit, 417, which acts as much on the first microwave changeover switch 43 as on the second, 49, in order to obtain at least four different successive output signals, each of the abovementioned signals corresponding to each of the possibilities for connection of the two respective microwave changeover switches 43 and 49.

Hence, the first microwave changeover switch 43 comprises 2 input channels, while the second microwave changeover switch 49 comprises at least 2 input channels.

As will be observed in FIG. 2, the output, 411b, of the circulator 411 is linked to a microwave amplifier, 414, and the output of the microwave amplifier 414 is itself linked to a microwave detector, 415, with one input, marked 415b. The output, 415a, of the microwave detector 415 is linked to a sampling circuit 416, which delivers sampled values of the signals delivered by the microwave detector 415 by means of an output, 418, to the calculation and display console 7.

It will moreover be noted that the calculation and display console 7 allows, under the control of the control and synchronization circuit, 417, in particular, calculating, on the basis of the sampled values of the 4 successive abovementioned signals, the temperature in the region of the applicator in question, independently of the reflection coefficient of the applicator with respect to the area Z to be treated and of the losses in the microwave changeover switches and the interconnection cables.

It will be noted in particular that the value of the absolute temperature T of the region Z to be treated may be determined, on the basis of reference temperatures T1 and T2 which are known from the resistive elements connected to the second changeover switch 49, and represented by the references 47 and 48 in FIG. 2, and of the voltages available at the output of the sampler 416, this independently of the reflection coefficient r and of the width P of the pass band of the device.

For a more detailed description of the operation of a dual-reference radiometer such as that incorporated in the system which is the subject of the present invention and represented in FIG. 2, reference may be advantageously had to the French Patent Application No. 89 10148, filed in the name of the applicant on Jul. 27, 1989 and published on Feb. 1, 1991 under No. 2 650 390.

A preferential embodiment of the system in accordance with the subject of the present invention incorporating a dual-temperature-reference radiometer 4, which is particularly advantageous, will now be described in relation to FIG. 3a.

In a general way, it will be noted that the temperature measurement device constituted by the dual-temperature-reference radiometer 4 is composed mainly of the microwave changeover switch 43 represented in FIG. 2 with two channels, this changeover switch possibly being produced by a changeover switch of MICROWAVE model F 9120 or F 9220 general type tuned to the working frequency linking the input 411a of the circulator, either to the antenna of the applicator 30 or 31, or to the short-circuit 42 previously described in the description.

The link cables between the microwave changeover switch 43 and the corresponding applicator, the short-circuit 42 and this same microwave changeover switch must be of very low loss and of equal length, marked B1 on FIG. 3a, so as to exhibit the same coefficients of transmission of the corresponding signals.

The circulator 411 is a wide band circulator, the frequency band of the latter being at least equal to 1 GHz around the central frequency of the system, which can be taken to be equal, for the dual-reference radiometer 4, to 1.2 or 3 or 9 GHz. The abovementioned circulator may be, for example, a 3-channel circulator of NARDA COS 2652 type or the like.

Finally it will be noted that the microwave changeover switch 49 makes it possible to switch over the 2 noise sources at reference temperature 47, 48, which supply the reference temperatures TRj, with j taking the values 1 or 2.

A combination of the changeover positions of the microwave changeover switches 43 and 49, as described by the table given below, makes it possible to obtain the various signals S1, S2 and S3, S4 at the output of the sampling unit 416.

| Change- | Changeover Switch Position | |
|---|---|---|
| over Switch | 49 49a | 49b |
| Position | 43 | |
| | 43a   S2 = K.P.[r.TR1 + (1 − r)T] | S4 = K.P.[r.TR2 + (1 − r)T] |
| | 43b   S1 = K.P.TR1 | S3 = K.P.TR2 |

In the relations giving the values of the abovementioned signals, it will be noted that K designates the Boltzmann's constant, P designates the value of the pass band of the dual-reference radiometer 4 and r designates the value of the coefficient of reflection of the applicator 30 or 31 in question. The abovementioned sampled signals are then stored in the region of the microcomputer constituting the calculation and visual display console 7 and a linear combination of these signals obtained on the basis of the expressions below:

$$Va \simeq S1 - S2$$

$$Vb \simeq S3 - S4$$

makes it possible to obtain the value of the absolute temperature T of the area Z to be treated by the relation:

$$T = \frac{Va\,TR2 - Vb\,TR1}{Va - Vb}.$$

Hence it will be noted that the value of the absolute temperature T of the region Z to be treated is thus calculable on the basis of the reference temperatures TR1 and TR2, and this can be done completely independently in relation to the coefficient of reflection r and to the width P of the pass band of the dual-reference radiometer.

For a more detailed description of the dual-reference radiometer 4 employed in the system which is the subject of the present invention, reference may usefully be had to the description of the French patent application already mentioned and previously incorporated in the description of the present application by way of reference.

As has further been represented in FIG. 3a, the dual-reference radiometer 4 comprises a sampling module, 420, with three outputs. A first output, 421, of the sampling module 420 is linked to an electrical short-circuit in the microwave frequency band of the radiometer 4, a second output, 422, of the sampling module is linked to a first calibrated resistor of defined value in the frequency band of the radiometer, this resistor being taken at first to a temperature T1 of defined value. Finally, the third output 423 of the sampling module 420 is linked to a second calibrated resistor of the same defined value in the frequency band of the radiometer 4, this second resistor being taken in operation to a defined temperature T2.

It will be noted that, advantageously, the microwave changeover switch 43 of the dual-reference radiometer, as represented in FIG. 2, may then be replaced by a multichannel microwave changeover switch marked 643, the reference 643 in fact designating a combination of the two-channel microwave changeover switch 43 of FIG. 2 and of the multichannel microwave changeover switch 6 of FIG. 1, for example.

It will obviously be noted that the multichannel microwave changeover switch 643 makes it possible to selectively link, to the input forming measurement input of the dual-reference radiometer 4, either one of the microwave applicators 30 or 31, or one of the outputs of the sampling module. Hence, the multichannel microwave changeover switch 643 is a changeover switch with 6 inputs and one output, the 6 inputs being marked 643a, b, d, e, f, g, and the output being marked 643c by analogy with the microwave changeover switch 643 of FIG. 2. The inputs 643d, e, f, are linked respectively to the first 421, second 422, and third 423 output of the three-output sampling module 420. Furthermore, the inputs 643g, a and b, are linked respectively to the terminals 5a, 5d, of the multichannel changeover switch 5 as represented in FIG. 1 and to the short-circuit 42.

It will thus be noted that, in the context of FIG. 3a, the measurement input of the dual-reference radiometer 4 is produced either by the terminal 643g, or by the terminal 643a of the multichannel changeover switch 643.

It will thus be noted advantageously that the interconnection cables between the multichannel changeover switch 643, the previously described inputs of the latter and their various linking points may advantageously consist of cables of equal length marked B1 as shown in FIG. 3a. The length of the cables is thus chosen so as to strike a balance for the device as far as the losses introduced by the abovementioned connection cables are concerned.

A description of the operating mode allowing the implementation of an automatic calibration of a system for the internal thermal treatment of specific bodies, which is the subject of the present invention, according to the embodiment of FIG. 3a will now be given in connection with FIGS. 3b to 3d.

In the calibration process implemented, it will be noted that the calibration can be carried out on the basis of one of the applicators 30, 31 in a similar way. In any case, the measurement input of the dual-reference radiometer 4 will then be considered as the terminal 643c of the multichannel microwave changeover switch 643, which can be interconnected to one of the input terminals previously described in the description of the multichannel changeover switch 643.

The calibration process, in accordance with a subject of the present invention, then consists advantageously, as illustrated in connection with FIG. 3b, firstly in connecting the measurement input of the dual-reference radiometer to the first output 421 of the calibration module 420, the measurement input of the dual-reference radiometer 4 then being short-circuited. The second multichannel changeover switch 49 of the dual-reference radiometer 4 is then connected to the first, TR1, then to the second, TR2, temperature reference as illustrated in FIG. 3b. The corresponding values Vo1 and Vo2 of the signal delivered by the sampling circuit 416 are then measured and stored in memory.

The calibration process consists, secondly, as shown in FIG. 3c in connecting the measurement input of the dual-reference radiometer 4 to the second output 422 of the sampling module 420. The abovementioned measurement input is then connected to the resistor of defined value taken to the temperature T1 of defined value. The second multichannel changeover switch 49 is then connected to the first TR1, then to the second TR2 temperature reference. The corresponding values V11 and V12 of the signal delivered by the sampling circuit 416 are then measured and stored in memory.

Thirdly, as shown in FIG. 3d, calibration process consists in connecting the measurement input of the dual-reference radiometer to the third output 423 of the sampling module 420. The abovementioned measurement input is then connected to the resistor of defined value taken to the temperature T2 of defined value. The second multichannel changeover switch 49 of the dual-reference radiometer 4 is then connected to the first TR1, then to the second TR2, temperature reference. The corresponding values V21 and V22 of the signal delivered by the sampling circuit 416 are then measured and stored in memory.

It will be noted that the abovementioned memory-stored values each satisfy a relation of the form:

$$V_{ij} = K.\Delta F(a.K2 \times T \times (1-\rho) + T_{cab}.K2(-1-a).(1-\rho) - a^2\rho + TR_j(a^2 + K^22.\rho - K^21)).$$

It will be noted that in this relation:

$V_{ij}$ designates each abovementioned memory-stored value,

K designates the product of the gain G of the chain and Boltzmann's constant KB, $\Delta F$ designates the pass band of the dual-reference radiometer, $TR_J$ designates either the first TR1, or the second TR2 reference temperature, for j taking the values 1, 2 respectively, K1 and K2 designate the loss coefficients of the first microwave changeover switch 643 for the channels 1 and 2, a designates the losses in the cable making it possible to provide the cable link between measurement input of the dual-reference radiometer 4 and various inputs of the calibration module 420, Tcab designates the temperature of the link cable, with $\rho=0$, upon interconnection of the input of the dual-reference radiometer 4 to the second or third input 422, 423 and to the corresponding resistor of defined value of the calibration module 420 and $\rho=1$ upon interconnection of the input of the dual-reference radiometer 4 to the first input 421 and to the corresponding short-circuit of the calibration module 420.

The linear equations having the abovementioned memory-stored values Vij and the parameters of the abovementioned device may then be resolved digitally by means of the microcomputer constituting the calculation and display console 7 for determining the abovementioned parameters.

It will be noted, in general, that the various previously described steps of the calibration process may be permutated without departing from the scope of the present invention by reason especially of the fact that the relationships satisfied by the previously mentioned sampled voltage values Vij are linear, the physical parameters of the device being considered as independent variables.

It will be noted moreover, that the previously described calibration process may be implemented more particularly in the context of a calibration carried out in the laboratory in the manner described below when the two temperatures T1 and T2 to which the resistors of the calibration module 420 are taken are adjustable. In such a case, the calibration process may consist, advantageously:

firstly, in carrying out the step described firstly above in the description in the context of the calibration process.

Secondly, the steps previously described secondly and thirdly in the previous calibration process are carried out in relation to the reference temperatures TR1, TR2 successively, the adjustable temperature T1, T2, that is to say one of the two, being adjusted progressively so as to obtain a nil value for the corresponding values V11, V12 or V21, V22, delivered by the sampling circuit 416, for corresponding values known as zero temperatures, and marked respectively TZ1, TZ2, of the adjustable temperatures T1 or T2. Each zero temperature satisfies a relation of the type:

$TZj=(TRj.K1^2-Tcab.K2(1-a)+Voj)/(a.K2.K.\Delta F)$.

It will be noted that in this relation, j needless to say designates the index which may take the value 1 or 2 relative to the temperature reference actually used.

Similarly, K designates the product of the gain of the chain with the Boltzmann's constant KB.

It will be noted in the embodiment of FIG. 3a, the existence of the short-circuit 42, which is linked to the terminal 643b of the multichannel changeover switch 643, and of the short-circuit linked to the output 421 of the calibration module 420 implies the use of identical connecting cables, so as to bring about good physical balancing of the whole of the system. This balancing may be checked by comparison of sampled signals or voltages delivered by the sampling module 416, a value which is identical or substantially identical, to within measurement errors, of these signals delivered respectively by the sampled detection module 416 when switching to one or the other of the short-circuits indicating satisfactory balancing of the whole of the device.

Needless to say, as represented in FIG. 3e, one of the short-circuits may be removed, and, in this case, the multichannel microwave changeover switch 643 comprises one less input terminal, the short-circuit of the calibration module 420 and the first output 421 of the latter being, for example, removed. The calibration module 420 is then a two-output, 422 and 423, calibration module. Such a modification of the calibration module makes it possible in fact to produce a calibration module equivalent to that previously described in the description.

A more detailed description of a system for the internal thermal treatment of specific bodies in accordance with the subject of the present invention, more particularly suitable for the treatment of living tissues, in particular for the treatment of an adenoma of the prostate, will now be described in connection with FIG. 4.

As it has been represented in the abovementioned figure, the system which is the subject of the present invention comprises, advantageously, a first, 20, a second, 21, and a third, 22, transmission channels connected in parallel at the output of the microwave energy generator 1. A first, 30, and a second, 31, microwave applicator (sic) are provided, the first microwave applicator, 30, a rectal applicator, being linked, on the one hand to the output of the first channel 20, and, on the other hand, selectively to the output of the second channel, 21, or to the measurement input of the dual-reference radiometer 4 by means of a first and of a second multichannel microwave changeover switches, which are marked 5 and 6 in FIG. 4.

The second applicator, 31, a urethral applicator, is also selectively linked to the output of the third channel, 22, or, on the other hand, to the measurement input of the dual-reference radiometer by means of the first multichannel changeover switch 5 and of the second multichannel changeover switch 6.

It will be noted in particular that the first and second applicators 30, 31, are thermostatically controlled by means of a thermostatic control unit 8, which delivers a thermostatic control fluid to each of the abovementioned applicators. The thermostatic control unit will not be described in detail, as it corresponds to a constituent element known to the person skilled in the art.

It will, however, be noted that the second and third channels, 20, 21 each comprise a programmable phase shifter circuit, 210, 211, making it possible to phase shift the carrier wave of the microwave energy transmitted to the corresponding applicators, 30, 31.

It will further be noted that each channel 20, 21, 22, comprises a corresponding amplifier, 201, 211, 221, for the microwave energy, this amplifier being capable of playing the role of modulator so as to modulate the carrier wave according to a series of pulses of defined mark-space ratio, the mark-space ratio thus making it possible to determine the microwave energy actually applied in the region of each applicator. The previously mentioned microwave modulator amplifier devices will not be described in detail, as it (sic) can be represented by any modulator amplifier device normally available on the market for providing amplification and modulation of microwave energy, whose frequency f0 is substantially equal to 915 MHz.

A more detailed description of the urethral applicator 31 will be given in connection with FIGS. 5a to 5c.

According to the abovementioned figures, the urethral applicator comprises, in a probe of the Foley probe type, a wire antenna 311 connected to the corresponding changeover switch via a microwave connector, 3110a, and a coaxial cable, 3110b. The urethral applicator also comprises a water inlet tube, 312, and a water outlet tube, 313, in the probe, the water being delivered by the thermostatic control unit 8 and thus making it possible to provide a flow of water playing the role of thermostatic control fluid.

As will be noted from observation of FIG. 5b, the wire antenna constituted by the microwave cable 311 comprises a stop, 3113, arranged at a suitable distance from the end of the abovementioned wire antenna, this stop being intended to adjust the effective length of the wire antenna in the Foley type probe. The stop 3113 may be produced from a plastic material, for example, bonded to the microwave cable 3110b.

As it has also been represented in FIG. 5b, it will be noted that the wire antenna 311 is formed by the coaxial cable exhibiting successively at its end in the direction of forward propagation of the microwave energy, a part, 3111, of length h over which the shielding of the coaxial cable has been removed, the central core of the coaxial cable being covered over this part by the dielectric material of the cable. A part, 3112, of length h' is formed by the central core of the completely bared coaxial cable. The lengths h and h' are determined on the basis of the frequency f0 of the carrier wave of the microwave energy and of the dimensions of the area to be heated.

It will be noted that, with a view to serving for applications in gynecology, the applicator described in relation with FIGS. 5a and 5b may advantageously be modified as represented in FIG. 5c.

In this case, the parts of length h and h' are covered over by a cap, 3114, made of dielectric material. The cap exhibits an oblong shape so as to provide impedance matching of the wire antenna to the surrounding tissue.

A detailed description of an operating mode, i.e. of a utilisation mode of the system which is the subject of the present invention as represented in FIG. 4, more particularly in the case of treatment of an adenoma of the prostate, will be given in connection with FIGS. 6a to c.

In the abovementioned case, the treatment process proper comprises, after implantation of the rectal and urethral applicators 30, 31, as represented in FIG. 6a in the corresponding appropriate physiological cavity or cavities, in particular steps consisting in emitting, to the abovementioned applicator or applicators 30, 31 a defined microwave energy level and modulating the relative phase of the carrier wave of the microwave energy transmitted by two consecutive channels according to a defined modulation program in order to modulate the energy level transferred to the region of the area to be treated Z.

Needless to say, from observation of FIG. 6a, it will be understood that the area Z to be treated encompasses the prostate subjected to the treatment, this area Z being situated between the two applicators after implantation of the latter.

As it has been represented in FIG. 6b, the phase modulation, that is to say the choice of a value $\phi$ of the relative phase of the electric field radiated by the first and the second applicators, for example 30, 31, makes it possible to generate, in the region of the are Z to be treated, a resultant electric field, ER, whose amplitude satisfies the relation $ER = 2E.\cos\phi$, which has the effect of allowing application of microwave energy proportional to the square of the abovementioned amplitude, i.e. proportional to four times the amplitude of the electric field radiated by one of the applicators. There is thus obtained a very large dynamic range of the energy actually applied to the region of the area Z to be treated, this dynamic range being in a ratio of 2 with respect to the dynamic range of energy applied in the absence of modulation. The programmed modulation of the relative phase of the carrier wave of the microwave energy and thus of the electric field radiated by each applicator can be carried out continuously or in discrete increments, and this can be done so as to modulate the quantity of energy applied to the area Z to be treated and finally the temperature increase applied to the abovementioned area.

In FIG. 6c is represented, by way of nonlimiting example, a change law for the temperature rise of the area Z to be treated towards a constant temperature marked Tass, which can be maintained by periodic emission by one and/or by the other applicator 30, 31.

It will be noted, needless to say, that, on the one hand, the servo controlled temperature Tass as well as the slope p, or the law of convergence towards this servo controlled temperature, are defined by the practitioner on the basis of the application in question.

According to one advantageous characteristic, the slope p or the law of convergence towards the servo controlled temperature may be chosen in such a way as to correspond to an increasing monotonous function of the temperature as a function of time by temperature increment $\Delta T$ lying between 0.8° C. to 1.2° C. per minute.

Preferably, and according to a particularly advantageous aspect of the system which is the subject of the present invention, the radiated power, which corresponds to a radiated maximum radiated (sic) electrical power of 50 watts may then be adjusted so as to satisfy, for the power increments applied by each successive radiation, the relation:

$\Delta P = M.\Delta T + N.\Delta T$ theoretical/$\Delta T$ achieved.

It will obviously be noted that in the abovementioned relation, $\Delta P$ represents the power increment delivered by one and/or the other of the applicators 31 or 30, M represents a coefficient of proportionality depending on the area, and finally on the organ to be treated, and on the applicators used, $\Delta T$ represents the temperature increase with respect to the previous measurement by means of the dual-reference radiometer, N represents a coefficient of proportionality depending also on the organ and on the applicators used as well as on the temperature increase law chosen by the practitioner, $\Delta T$ theoretical is a value stored in memory within the microcomputer constituting the calculation and display console 7, these memory-stored values corresponding to the application in question and constituting, for this application, a data base available to the practitioner, and, $\Delta T$ achieved being the temperature increase measured by the dual-reference radiometer between two temperature measurements separated by the application of a given quantity of microwave energy.

It will obviously be noted that the values of M and N as well as values which are representative of the temperature increase law are incorporated into the abovementioned data base, the whole being available to the practitioner.

It will be noted in particular that for given phase shift values, the hottest point of the area Z treated moves either in front of the urethra or behind the rectum, having regard to the thickness of the prostate. Hence, for a prostate having a volume determined by ultrasound, it is then possible to calculate the various phases and the ratio of the microwave powers radiated by each of the channels in order to obtain maximum thermal effectiveness. By way of non-limiting example, when the three channels deliver an in-phase microwave power, the powers delivered by each of the channels being identical, the hottest area is situated substantially midway between the urethra and the rectal wall.

According to another treatment mode, treatment may consist in varying, as a function of time, the phase of the carrier wave delivered by each of the channels and in particular by two consecutive channels, either continuously by phase which is variable between 0° and 180°, or with fixed phase shift values, for example.

Hence, a treatment mode may consist for:

| t = 0 | urethral applicator 31 | phase = 0° |
|---|---|---|
| | rectal applicator channel 21 | phase = 0° |
| | rectal applicator channel 20 | phase = 120° |
| t = 4 seconds | | |
| | cyclic permutation | urethral phase = 120°, |
| | the other phases being taken to be equal to 0°. | |

It will be noted that the choice of the sequencing time is a function of the geometry and of the volume of the organ to be treated and hence of the area Z subjected to the hyperthermia. This sequencing, in order to produce an optimum thermal effect, according to a theoretical study carried out, should lie between 3 and 9 seconds.

It will be noted that the multichannel microwave changeover switches make it possible to switchover the various applicators, the latter operating either as microwave energy applicators, or as temperature sensors or detectors. For example, in certain cases, it is preferable to heat the tissues with one of the applicators, for example the rectal applicator, and to measure the temperature by radiometry by means of the urethral applicator and/or one of the channels of the rectal applicator or vice versa.

Thus a particularly high performance system has been described for the internal thermal treatment of specific bodies by application of microwave energy, this system, by reason of the use of a dual-temperature-reference radiometer, making it possible to very precisely determine the temperature of an area to be treated. Furthermore, the system which is the subject of the present invention exhibits very great flexibility in use, by reason of the fact that the microwave applicators are also used as temperature sensors at the point of radiation of the abovementioned microwave energy. The very great flexibility in use of the system which is the subject of the present invention is also brought about by virtue of the implementation of a phase modulation of the microwave energy delivered by two consecutive applicators, this phase modulation especially making it possible for the practitioner to bring about a movement of the hottest point of the area treated, and hence therefore to envisage specific treatments of the abovementioned area.

We claim:

1. System for the internal heat treatment of specific bodies by application of microwave energy to an area to be treated, said system comprising a generator of microwave energy at a first defined frequency, at least two transmission channels for transmitting said microwave energy emitted by said generator, each transmission channel generating a microwave treatment signal modulated in amplitude according to a defined, periodic modulation law at a second defined frequency, a carrier wave of said microwave energy of said two transmission channels exhibiting a phase shift, at least one microwave applicator associated with each of said at least two transmission channels for applying said microwave treatment signal delivered by said transmission channels at separate points in the vicinity of the area to be treated, and means for calculating and displaying microwave powers radiated and instantaneous temperatures of said separate points, wherein said system further comprises:

a dual-temperature-reference radiometer selectively interconnected to each of said at least one microwave applicator, for measuring an absolute temperature of a separate point of said separate points associated with an interconnected microwave application;

a three-output calibration module linked to said dual-temperature-reference radiometer, a first output of said calibration module being linked to an electrical short-circuit in a microwave frequency band of said radiometer, a second output of said calibration module being linked to a first calibrated resistor of defined value in said microwave frequency band of said radiometer, said first resistor being brought, in operation, to a first temperature T1, and a third output of said calibration module being linked to a second calibrated resistor of said defined value in said frequency band of said radiometer, said second resistor being, in operation, brought to a second temperature T2; and a multichannel microwave changeover switch forming a measurement input of said dual-temperature-reference radiometer, said multichannel microwave changeover switch being selectively linked to either one of said microwave applicators associated with said transmission channels, or one of the outputs of said calibration module.

2. System according to claim 1, wherein said multichannel microwave changeover switch further comprises a first input channel, a second input channel and an output channel, said first input channel being connected to said electrical short-circuit, said dual-temperature-reference radiometer further comprising:

a first microwave changeover switch comprising two input channels and an output channel, one of said two input channels being connected to an output of said at least one microwave applicator., the other of said two input channels being connected to a microwave short-circuit, and said output channel of said first microwave changeover switch being connected to said second input channel of said multichannel microwave changeover switch;

a circulator with three successive channels comprising a first channel connected to said output of said multichannel microwave changeover switch, a second channel connected to an input of a microwave electronic treatment assembly, and a third channel constituting a reference input;

at least two internal temperature reference sources; and a second microwave changeover switch comprising at least two input channels each connected to an output of said at least two reference sources and an output connected to said reference input of said circulator, said microwave electronic treatment assembly comprising:

a synchronization control circuit means for controlling both said first microwave changeover switch and said second microwave changeover switch in order to obtain at least four different successive output signals, each of said at least four signals corresponding to each of at least four possibilities for connecting said two microwave changeover switches, said at least four possibilities including the selections of the following connections of said second and said first microwave changeover switch respectively, (1) an output of a first one of said at least two internal reference sources and said output of said at least one microwave applicator, (2) said output of said first one of said at least two internal reference sources and said microwave short circuit, (3) an output of a second one of said at least two internal reference sources and said output of said at least one microwave applicator, and (4) said output of said second one of said at least two internal reference sources and said microwave short circuit;

a microwave detector with an input connected by means of a microwave amplifier to said second channel of said circulator; and a sampling circuit connected at an output of said microwave detector for delivering sample values of signals delivered by said microwave detector to said calculating and displaying means, said calculating and displaying means, under the control of said synchronization control circuit means for calculating, on the basis of sampled values of said at least four successive output signals, a temperature in the region of said at least one microwave applicator, independently of a reflection coefficient value of said at least one microwave applicator with respect to the area to be treated and losses in said microwave changeover switches and in interconnection cables.

3. System according to claim 1, wherein in the case of the treatment of living tissue, said at least two transmission channels comprise three transmission channels, said system comprising:

a first, a second and a third transmission channels of said three transmission channels being connected in parallel at an output of said microwave energy generator;

said at least one microwave applicator comprising a first and a second microwave applicator, said first microwave applicator, a rectal applicator, being linked, on the one hand directly to an output of said first transmission channel and, on the other hand, selectively to an output of said second transmission channel or to a measurement input of said dual-temperature-reference radiometer by means of a dual switch and of said multichannel microwave changeover switch, said second microwave applicator, an urethral applicator, being selectively linked, on the one hand to an output of the third channel or, on the other hand, to said measurement input of the dual-reference radiometer by means of said dual switch and of said multichannel changeover switch.

4. System according to claim 3, wherein said first and second microwave applicators are thermostatically controlled.

5. System according to claim 3 wherein said second and third transmission channels each comprise a programmable phase shifter circuit for the carrier wave of the microwave energy transmitted to the corresponding applicators.

6. System according to claim 3 wherein said urethral applicator comprises, in a Foley probe type probe, a wire antenna connected to the corresponding multichannel changeover switch via a microwave connector and a coaxial cable, a water inlet tube and a water outlet tube in the probe, allowing a flow of water to be provided.

7. System according to claim 6, wherein the wire antenna comprises a stop arranged at a defined distance from an end of the wire antenna and making it possible to adjust the effective length of the wire antenna in the Foley type probe.

8. System according to claim 6, wherein said wire antenna is formed by said coaxial cable, said coaxial cable having a shielding and a central core covered with dielectric material and, at an end in a direction of direct propagation of the microwave energy, successively comprising:

a part of length h over which said shielding of said coaxial cable has been removed, said central core of said coaxial cable being, over this part, covered over by said dielectric material of said cable; and a part of length h' formed by said central core of the completely bared coaxial cable, the lengths h and h' being determined by said first defined frequency of the microwave energy.

9. System according to claim 8, wherein the parts of length h and h' are covered over by a cap of dielectric material, making it possible to provide impedance matching for the wire antenna.

10. A method for calibration of a system for the internal heat treatment of specific bodies by application of microwave energy to an area to be treated, said system comprising:

a generator for producing microwave energy at a first defined frequency;

at least two consecutive channels transmitting said microwave energy, each channel generating a microwave treatment signal modulated in amplitude according to a defined, periodic modulation law at a second defined frequency, a carrier wave of the microwave energy of said two consecutive channels exhibiting a phase shift;

at least one microwave applicator associated with each of said at least two consecutive channels for applying said microwave treatment signal delivered by said channel at separate points in the vicinity of the area to be treated;

means for calculating and displaying microwave power radiated and instantaneous temperatures of said separate points of the area to be treated;

a dual-temperature reference radiometer selectively interconnected to each of said at least one microwave applicator for measuring an absolute temperature of a separate point of said separate points associated with said at least one microwave applicator in the vicinity in the area to be treated;

a three-output calibration module linked to said dual-temperature reference radiometer, a first output of said calibration module being linked to an electrical short-circuit in the microwave frequency band of the radiometer, a second output of said calibration module being linked to a first calibrated resistor of defined value in the frequency band of the radiometer, and a third output of the calibration module being linked to a second calibrated resistor of said defined value;

a multichannel microwave changeover switch forming a measurement input of said dual-temperature-reference radiometer, said multichannel microwave changeover switch being selectively linked to either one of said at least one microwave applicator or one of said outputs of said calibration module, said dual-temperature-reference radiometer including;

a first microwave changeover switch comprising two input channels, one connected to an output of said at least one microwave applicator and the other to a microwave short-circuit circuit, and an output being connected to an input channel of said multichannel microwave changeover switch;

a circulator with three successive channels, a first channel being connected to an output of said multichannel microwave changeover switch, a second channel being connected to an input of a microwave electronic treatment assembly, and a third channel constituting a reference input;

at least two internal temperature reference sources, and second microwave changeover switch with at least two input channels each connected to an output of said at least two reference sources and an output of said second microwave changeover switch being connected to said reference input of said circulator;

said microwave electronic treatment assembly comprising a synchronization control circuit means for controlling both said first and said second microwave changeover switch, a microwave detector with an input connected through a microwave amplifier to an output of the circulator and a sampling circuit connected to an output of the microwave detector and delivering to said calculating and displaying means corresponding sample values, wherein said method for calibration comprises the steps of:

a) connecting said measurement input of said dual-temperature-reference radiometer to said first output of said calibration module, resulting in said measurement input of said dual-reference radiometer being short-circuited;

connecting said second microwave changeover switch of said dual-temperature-reference radiometer to a first temperature reference TR1 and then to a second temperature reference TR2; and measuring and storing values V01 and V02 of a signal delivered by said sampling circuit when said second microwave changeover switch is connected to said first temperature reference TR1 and said second temperature reference TR2, respectively;

b) connecting said measurement input of said dual-reference radiometer to said second output of said calibration module, resulting in said measurement input being connected to said first calibrated resistor at a first temperature T1;

connecting said second microwave changeover switch of said dual-reference radiometer to said first temperature reference TR1 and then to said second temperature reference TR2; and measuring and storing values V11 and V12 of said signal delivered by said sampling circuit when said second microwave changeover switch is connected to said first temperature reference TR1 and said second temperature reference TR2, respectively;

c) connecting said measurement input of said dual-reference radiometer to said third output of said calibration module, resulting in said measurement input being connected to said second calibrated resistor at a second temperature T2;

connecting said second microwave changeover switch of said dual-reference radiometer to said first temperature reference TR1 and then to said second temperature reference TR2; and measuring and storing corresponding values V21 and V22 of said signal delivered by said sampling circuit when said second microwave changeover switch is connected to said first temperature reference TR1 and said second temperature reference TR2, respectively; and d) solving the system of linear equations relating to stored values, said values each satisfying a relation of the form:

$Vij = K.\Delta F$ $(a.K2 \times T \times (1-\rho) + Tcab.K2 (1-a).(1-\rho) - a^2\rho + TRj (a^2 + K^22.\rho - K^21)$.

where i∈ and j∈

Vij designates each of said stored values;

K designates a product of gain G of the chain, with the Boltzmann's constant KB;

$\Delta F$ designates a pass band of said dual-temperature-reference radiometer;

TRj designates either the first temperature reference TR1 or the second reference temperature TR2 for j=1 and 2 respectively;

K1 and K2 designate electrical loss coefficients of the first microwave changeover switch of said dual-temperature-reference radiometer for said consecutive channels under consideration;

a designates electrical losses in a cable linking said measurement input of the dual-reference-temperature radiometer and said inputs of said calibration module;

Tcab designates a temperature of said cable, with $\rho=0$ upon inter-connection of the input of said radiometer to said second or said third input and, thus, to a first or second calibrated resistor, respectively, of the calibration module, and $\rho=1$ upon interconnection of the input of said radiometer to said first input and, thus, to said electrical short-circuit of said calibration module.

11. The method according to claim 10, wherein the two temperatures T1 and T2 to which said resistors of said calibration module are brought, being adjustable, said calibration process comprising the steps of:

a') carrying out the preceding step a), b') carrying out the preceding steps b) or c) relative to the reference temperatures TR1, TR2 successively, progressively adjust the adjustable temperature T1 or T2 so as to obtain a nil value for the corresponding values V11, V12 or V21, V22 delivered by said sampling circuit for corresponding values, called zero temperatures, TRZ1, TRZ2, of said adjustable temperatures T1, T2 respectively, each zero temperature satisfying a relation of the type;

$TRZj = (TRj.K1^2 - Tcab.K2(1-a) + Voj)/(a.K2.K.\Delta F)$, in which j designates the index which can take the value 1 or 2, $K = G.KB$.

12. Method of treating an adenoma of the prostate by application of microwave energy to a given area of the prostate comprising the steps of:

implanting a rectal applicator and a urethral applicator in the corresponding physiological cavities; selectively supplying said rectal applicator with said microwave energy by one of two consecutive channels, wherein said two phase shifted channels comprise a phase-shifted channel and a nonphase shifted channel, p1 supplying said urethral applicator with microwave energy by said phase shifted channel, said given area of the prostate to be treated being situated between said rectal and said urethral applicators, subjecting a carrier wave of the microwave energy transmitted by said two consecutive channels to a relative phase shift;

emitting a defined microwave energy level to at least one of said applicators; and modulating said relative phase of the carrier wave of the microwave energy transmitted by said two consecutive channels in order to modulate an energy level transferred to the region of the area to be treated thereby allowing the area to reach a servo controlled temperature for the latter, according to a given slope p or convergence law.

13. Method according to claim 12, wherein said slope p or convergence law is chosen in such a way as to correspond to an increasing monotonous temperature function, as a function of time, by temperature increments lying between 0.8° C. and 1.2° C. per minute.

14. Method according to claim 12, wherein the modulation of the relative phase of the carrier wave of the microwave energy transmitted by two consecutive channels is carried out either continuously by variable phase between 0° and 180°, or with fixed phase shift values.

* * * * *